(12) United States Patent
Caluser (10) Patent No.: US 10,512,448 B2
(45) Date of Patent: *Dec. 24, 2019

(54) THREE DIMENSIONAL MAPPING DISPLAY SYSTEM FOR DIAGNOSTIC ULTRASOUND MACHINES AND METHOD

(71) Applicant: Metritrack LLC, Villa Park, IL (US)

(72) Inventor: Calin Caluser, Glen Ellyn, IL (US)

(73) Assignee: Metritrack, Inc., Hillside, IL (US)

( * ) Notice: Subject to any disclaimer, the term of this patent is extended or adjusted under 35 U.S.C. 154(b) by 291 days.

This patent is subject to a terminal disclaimer.

(21) Appl. No.: 14/182,441

(22) Filed: Feb. 18, 2014

(65) Prior Publication Data

US 2014/0163376 A1    Jun. 12, 2014

Related U.S. Application Data (63) Continuation of application No. 12/288,478, filed on Oct. 20, 2008, now Pat. No. 9,439,624.
(Continued)

(51) Int. Cl.
  *A61B 8/00* (2006.01)
  *A61B 8/08* (2006.01)
  (Continued)

(52) U.S. Cl.
  CPC .............. *A61B 8/4263* (2013.01); *A61B 5/06* (2013.01); *A61B 8/00* (2013.01); *A61B 8/4245* (2013.01);
  (Continued)

(58) Field of Classification Search
  USPC ....................................................... 600/443
  See application file for complete search history.

(56) References Cited

U.S. PATENT DOCUMENTS

| 5,438,996 A | 8/1995 | Kemper et al. |
| 5,911,126 A | 6/1999 | Massen |

(Continued)

FOREIGN PATENT DOCUMENTS

| WO | WO 2004/098414 | * 11/2004 |
| WO | 2005099581 A1 | 10/2005 |

(Continued)

OTHER PUBLICATIONS

Pagoulatos et al., "Interactive 3-D Registration of Ultrasound and Magnetic Resonance Images Based on a Magnetic Position Sensor," IEEE Transactions on Information Technology in Biomedicine, vol. 3, No. 4, Dec. 1999, pp. 278-288.

*Primary Examiner* — Thomas J Hong
*Assistant Examiner* — Shahdeep Mohammed
(74) *Attorney, Agent, or Firm* — Ziolkowski Patent Solutions Group, SC (57) ABSTRACT

An apparatus, system, and method where the ultrasound transducer position registration is automated, calculates the position of each pixel in the ultrasound image in reference to the predetermined anatomical reference points (AR) and can store the information on demand. The graphic interface associated with the ultrasound image allows for the instant display of selected targets position coordinates relative to anatomical reference points, in the ultrasound images. This system would significantly reduce the ultrasound examination time, by eliminating the time consuming manual labeling of images and speeding up the target finding at subsequent examinations, enhance correlation capability with other diagnostic imaging modalities like CT scans, MRI, mammograms, decrease human errors and fatigue, provide an easy, uniform, method of communicating the target position among healthcare providers.

32 Claims, 8 Drawing Sheets

Related U.S. Application Data (60) Provisional application No. 60/999,789, filed on Oct. 19, 2007.

(51) Int. Cl.
*G06F 19/00* (2018.01)
*A61B 5/06* (2006.01)

(52) U.S. Cl.
CPC ............ *A61B 8/4254* (2013.01); *A61B 8/483* (2013.01); *G06F 19/321* (2013.01)

(56) References Cited

U.S. PATENT DOCUMENTS

| | | |
|---|---|---|
| 6,171,244 B1 | 1/2001 | Finger et al. |
| 6,203,497 B1 | 3/2001 | Dekel et al. |
| 6,261,247 B1 | 7/2001 | Ishikawa et al. |
| 6,390,982 B1 | 5/2002 | Bova et al. |
| 6,443,894 B1 | 9/2002 | Sumanawerra et al. |
| 6,500,118 B1 | 12/2002 | Hashimoto |
| 6,669,653 B2 | 12/2003 | Paltieli |
| 6,675,038 B2 | 1/2004 | Cupples et al. |
| 7,176,916 B2 | 2/2007 | Riaz |
| 7,220,955 B2 | 5/2007 | Brunfeld et al. |
| 7,229,411 B2 | 6/2007 | Slayton et al. |
| 7,238,158 B2 | 7/2007 | Abend |
| 7,244,230 B2 | 7/2007 | Duggirala et al. |
| 7,251,352 B2 | 7/2007 | Sauer et al. |
| 7,255,695 B2 | 8/2007 | Falwell et al. |
| 7,259,897 B2 | 8/2007 | Garlick et al. |
| 7,260,426 B2 | 8/2007 | Schweikard et al. |
| 7,639,895 B2 | 12/2009 | Sakas et al. |
| 2002/0049375 A1 | 4/2002 | Strommer et al. |
| 2004/0019274 A1* | 1/2004 | Galloway et al. ............ 600/425 |
| 2004/0106869 A1 | 6/2004 | Tepper |
| 2005/0020917 A1* | 1/2005 | Scherch ........................ 600/437 |
| 2005/0119569 A1* | 6/2005 | Ohtake ........................ 600/437 |
| 2005/0119570 A1* | 6/2005 | Lewis .................... A61B 8/483 600/437 |
| 2005/0129299 A1* | 6/2005 | Kreang-Arekul et al. ... 382/132 |
| 2005/0245817 A1* | 11/2005 | Clayton ................... A61B 5/06 600/424 |
| 2005/0251028 A1 | 11/2005 | Boese et al. |
| 2006/0020204 A1* | 1/2006 | Serra et al. ................... 600/437 |
| 2006/0241445 A1* | 10/2006 | Altmann et al. .............. 600/443 |
| 2006/0247918 A1 | 11/2006 | Schmidt et al. |
| 2007/0010743 A1* | 1/2007 | Arai .............................. 600/443 |
| 2007/0023671 A1 | 2/2007 | Britten |
| 2007/0083117 A1 | 4/2007 | Sakas et al. |
| 2007/0167698 A1* | 7/2007 | Lloyd .................. A61B 6/4441 600/407 |
| 2007/0167805 A1 | 7/2007 | Clement |
| 2007/0219448 A1* | 9/2007 | Seip ......................... A61B 8/06 600/454 |
| 2007/0225553 A1* | 9/2007 | Shahidi .................. A61B 5/064 600/103 |
| 2007/0239004 A1 | 10/2007 | Kakee et al. |
| 2007/0249967 A1* | 10/2007 | Buly .................... A61B 5/1121 600/595 |
| 2008/0081982 A1* | 4/2008 | Simon ................. G06F 19/3437 600/407 |
| 2008/0085042 A1 | 4/2008 | Trofimov et al. |
| 2008/0095421 A1 | 4/2008 | Sun et al. |
| 2008/0200808 A1 | 8/2008 | Leidel et al. |
| 2008/0221446 A1 | 9/2008 | Washburn et al. |
| 2008/0262338 A1 | 10/2008 | Paitel et al. |

FOREIGN PATENT DOCUMENTS

| | | | |
|---|---|---|---|
| WO | WO2005099581 | * | 10/2005 |
| WO | 2006008300 A1 | | 1/2006 |

* cited by examiner

THREE DIMENSIONAL MAPPING DISPLAY SYSTEM FOR DIAGNOSTIC ULTRASOUND MACHINES AND METHOD

I. CROSS REFERENCE TO RELATED APPLICATION

The present invention is a continuation of and claims priority to U.S. application Ser. No. 12/288,478, filed Oct. 20, 2008, which claims the benefit of U.S. Provisional Patent Application Ser. No. 60/999,789, filed Oct. 19, 2007, the disclosures of which are incorporated herein by reference.

II. TECHNICAL FIELD

The present invention relates to diagnostic ultrasound technology and, more particularly, to a diagnostic ultrasound system in which ultrasound probe position registration is automated, the position of each pixel in the ultrasound image in reference to predetermined anatomical reference points is calculated, and specified information is stored on command. Moreover, the system, during real time ultrasound scanning enables the ultrasound probe position and orientation to be continuously displayed over a body or body part diagram, thereby facilitating the storage of information.

III. BACKGROUND OF THE INVENTION

Ultrasound is an important imaging modality for medical diagnostic purposes and as a guidance tool for diagnostic or therapeutic procedures, like soft tissue needle biopsy, tumor ablation, etc. Ultrasound can be used over the entire human body and has certain advantages over other modalities, including, among others: the ability to locate and characterize medical problems; lower cost compared to modalities such as MRI and CT; real time operation; and, the lack of ionizing radiation with the known associated health risks.

Ultrasound imaging systems transmit sound waves of very high frequency (e.g., 1 MHz to 20 MHz) into the patient's body and the echoes scattered from structures in the patient's body are processed to create and display images and information related to these structures.

Ultrasound imaging can be applied to various regions or organs in the body.

For example, a breast ultrasound procedure involves the placement of an ultrasound transducer over a region of interest of the breast, with the radiologist or other medical professional (the "user") viewing a real-time ultrasound image output on a display. The ultrasound machine monitor usually displays relevant text and/or graphical information next to the ultrasound image for simultaneous viewing by the user. The user can freeze the display, and the corresponding image can be printed on a printer or stored in digital format.

Two dimensional ("2D") ultrasound imaging, the most common technique used today, represents a slice through the region of interest. Three-dimensional ("3D") ultrasound scanning is available; however, it is usually used in conjunction with 2D scanning techniques. Currently, most diagnostic studies are performed using 2 D scanning technique.

The vast majority of ultrasound guided biopsies and other invasive ultrasound guided invasive procedures done by free hand and other more automated modes use the ultrasound machine 2D display mode. Therefore, it is desirable to have a fast and accurate way to find the target during such invasive procedures.

It is important to accurately store positional annotations for later evaluation, since this is essential for final interpretation, diagnosis, and treatment. As digital storage and communication of medical information replace hard copy based storage and communication technologies, the accurate and consistent annotation of ultrasound and other medical images is critical. Correlation of ultrasound images with images of the same body region obtained with other modalities (MRI, CT, mammograms, PET, etc.) becomes increasingly important for medical diagnostic and therapeutic purposes. As a result, precise positional registration of the targets is important.

This importance is illustrated by noting that finding a small tumor can save a patient's life. The smaller the tumor is before treatment, the higher the probability of long term patient survival; however, a small tumor is difficult to find in a patient's body and differentiate from other structures in the same region. Many times a suspicious small finding can coexist in the same region with multiple benign findings (cysts, solid benign nodules, etc), which may create confusion during a follow up exam and may lead to missing the suspicious lesion. As imaging diagnostic devices provide ever greater detail and sub-millimeter resolution, accurate position registration and mapping of lesions is becoming increasingly important in order to take advantage of the increased capabilities.

Ultrasound procedures are highly dependent on the device user's experience and training. Position recording of certain findings is important, especially for the small targets and/or multiple targets. Most frequently, an ultrasound user will hold the ultrasound transducer in one hand and use the other hand to operate the ultrasound machine controls. It is desirable to obtain the instant recording of target coordinates seen in the ultrasound image in relation to the anatomical reference (for example, a nipple) and the simultaneous recording of the transducer position. Currently, the automated recording of the transducer position in real time scanning is limited due to the motion of the pre-selected anatomical reference secondary to body and transducer induced motion. Therefore, it is desirable to continuously update the position of the anatomical references, or landmarks, and apply the correction to the obtained measurements.

The American College of Radiology (ACR) recommends that all ultrasound images be properly labeled. For example, for breast ultrasound images, the position, in hourly format or other format, and distance from nipple should be displayed with each diagnostic image containing significant findings. Currently, ultrasound findings are manually labeled by an operator, which is time consuming and prone to errors. Manual labeling involves the typing of an approximate position in the organ or part of the body, since an accurate position registration is time consuming and, importantly, difficult for the user.

Although multiple ultrasound guidance systems and devices already exist, they do not offer a practical and accurate solution to mapping patient findings in 2D or 3D images in relation to set anatomical reference point(s), which is operator independent during a routine examination, with real time correction for the patient's motion. It would be beneficial, therefore, to obtain the accurate position of selected targets in the ultrasound images in relation to set anatomical reference point(s) with the corresponding ultrasound transducer position and orientation by selecting the target in the ultrasound image at the time of examination or at a later date in the stored images with attached positional information. The present invention provides such an advance to the art.

IV. COPYRIGHT & LEGAL NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

V. OBJECTS AND ADVANTAGES OF THE PRESENT INVENTION

It is an object of the present invention to significantly reduce the time of the examination by eliminating the time consuming manual labeling of images and speeding up the target finding at subsequent examinations.

It is a further object of the present invention to obtain the accurate position of selected targets in ultrasound images in relation to set anatomical reference point(s) with the corresponding ultrasound transducer position and orientation by selecting the target in the ultrasound image at the time of examination or at a later date in the stored images with attached positional information in both 2D or 3D imaging techniques.

It is a further object of the present invention to enhance correlation capability with other diagnostic imaging modalities like CT scans, MRI, mammograms etc.

It is yet a further object of the present invention to eliminate or minimize errors due to inaccurate position labeling, therefore reducing the risk of costly lawsuits due to missed diagnosis and decrease the number of callbacks for the patients for repeat examination.

One advantage, among the many that will be appreciated by those skilled in the arts, is that the present invention provides an easy, uniform, method of communicating the target position among healthcare providers by guiding the ultrasound to a previously recorded target through following the real time display of the ultrasound transducer position in relation to the target coordinates from a previous examination.

VI. SUMMARY OF THE INVENTION

The present invention provides an apparatus and method of use for automated ultrasound probe position registration, calculating the position of each pixel in the ultrasound image in reference to the predetermined anatomical reference points (AR), and storing selected information on demand. The present invention further enables, during real time ultrasound scanning, continuous ultrasound probe position and orientation display, which display be permanently stored in the system's memory at the users command.

The Present invention comprises a hardware/software application and real time commercial 3D position registration system interfaced with an ultrasound machine.

After initial calibration and selection of one or more anatomical reference (nipple, umbilicus etc), positional information associated with each individually recorded image frame or each image in a cine loop is stored with the corresponding image. Using a pointing device with the system display, spatial numerical coordinates of the selected pixel or region, including the distance from the anatomical reference, depth, angle to the body axis and a graphical representation, are displayed next to the ultrasound image. Also displayed are the real time position of the ultrasound probe and target position in a diagram shown next to the real time ultrasound image, providing orientation help for the ultrasound operator.

Each ultrasound saved image or set of images in a cine loop will have attached the positional information corresponding to each pixel in the ultrasound frame and the diagram with the body part with the ultrasound transducer position and orientation in reference to the anatomical reference(s) and position of a target pixel(s), if any are selected. Other body parts or regions can be recorded with corresponding anatomical reference points, ex.: liver with umbilicus, neck with thyroid cartilage etc. Target pixel selection can be made at the time of the image capture, before saving the image, or at a later time at the review station.

During future examinations, the user is guided to the target by entering the target coordinates obtained at the previous examination, display the target in the body diagram and adjust the transducer position in the real time body diagram to overlap the target.

For the accurate automated recording of body targets and transducer position related to certain anatomical references, a user continuously obtains positional information from the preset anatomical references and the motion correction instantly applied to the transducer positional coordinates.

This is achieved by continuously monitoring the preset anatomical reference point(s) position, which in the preferred embodiment can be achieved with a magnetic sensor placed next to the anatomical reference on the skin. In an alternate embodiment the anatomical reference tracking can be obtained with an overhead tracking system using digital infrared or optical cameras with or without skin markers. In this embodiment, one camera can be used, or two or more cameras can be also used to achieve a three dimensional stereoscopic effect.

There has been outlined, rather broadly, the more important features of the invention in order that the detailed description thereof that follows may be better understood, and in order that the present contribution to the art may be better appreciated. There are, of course, additional features of the invention that will be described hereinafter and that will form the subject matter of the invention.

VIII. DETAILED DESCRIPTION OF THE PREFERRED EMBODIMENT

Before explaining the preferred embodiment of the present invention in detail, it is to be understood that the present invention is not limited in its application to the details of arrangements of the components set forth in the following description. As will be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Figure 1:
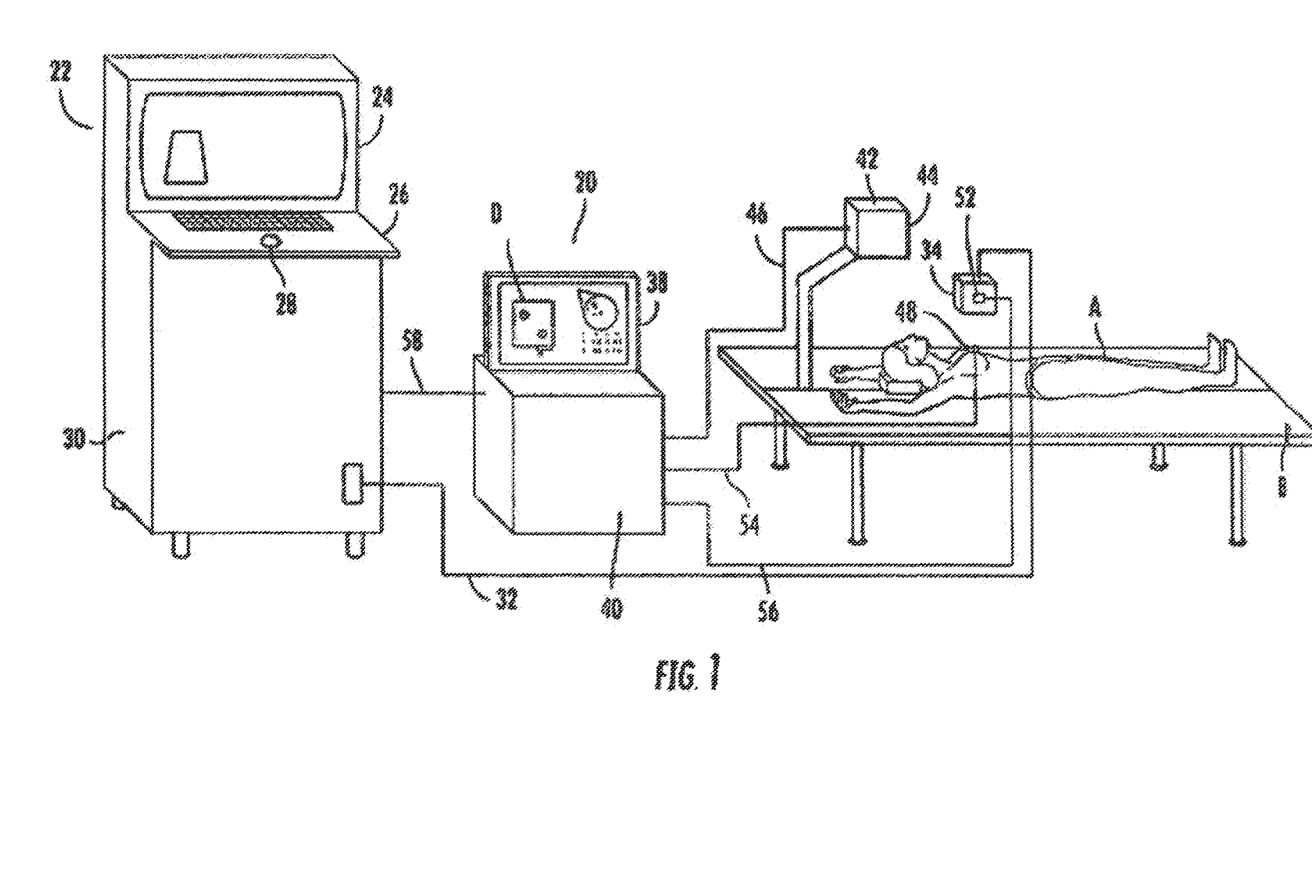
FIG. 1 depicts an overview illustration of the inventive apparatus placed in an ultrasound system.

Turning to FIG. 1, an over view of the physical aspects of an ultrasound device employing the inventive apparatus 20 is seen. Ultrasound machine 22 is a standard device including display 24, interface with keyboard 26 and pointer 28, chassis containing operating hardware (not seen) 30, transducer connecting cord 32, and transducer 34.

Inventive apparatus (also referred to as three dimensional mapping display, or TDMD) 20 is depicted and comprises TDMD display 38, TDMD Chassis 40 containing hardware (also referred to as a "processor") and software (not seen; described in detail below), 3D magnetic tracking member 42 with the transmitter 44 connected to TDMD 20 by 3D magnetic tracking member cord 46, first magnetic sensor 48 connected to TDMD 20 by first magnetic sensor cord 54 and second magnetic sensor 52 connected to TDMD 20 by second magnetic sensor cord 56.

For completeness in explaining FIG. 1, Patient A is situated on examining table B.

Figure 2:
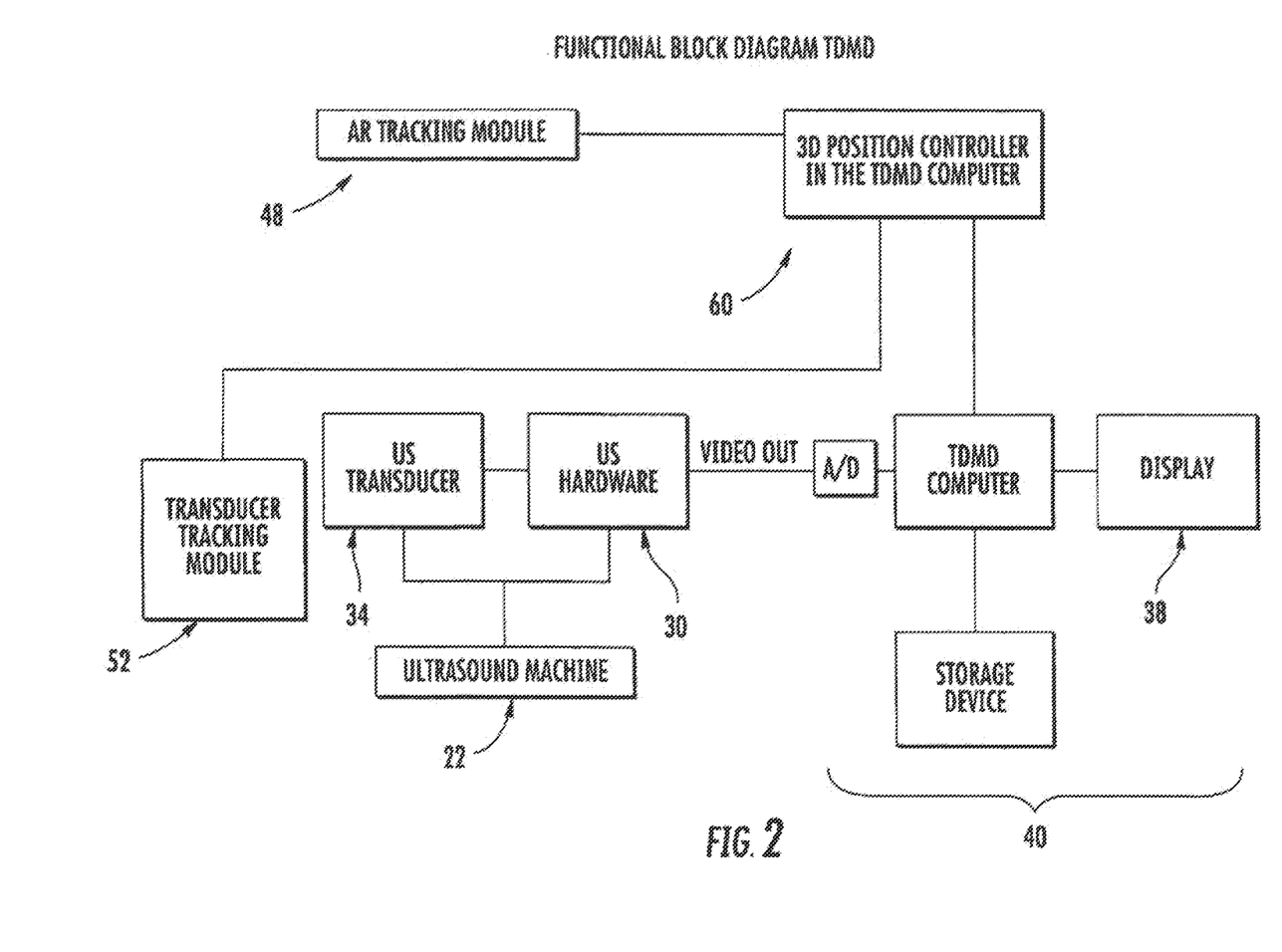
FIG. 2 illustrates the functional block diagram for the inventive device preferred embodiment with a magnetic sensor used for anatomical reference tracking.

Turning to FIG. 2, a block diagram illustrating the various general working aspects of inventive device 20 are shown. First magnetic sensor 48 and second magnetic sensor 52 provide the positional information to the TDMD 20 3D position board/module 60 (not seen). Video output 24 from ultrasound device 22 is digitized by the dedicated TDMD module/board 40. It should be noted that the analog to digital image conversion is not needed if the ultrasound machine can be interfaced and it can directly provide the digital images to the TDMD 20.

TDMD can continuously track one or several anatomical reference markers or positional body markers, which can increase the overall accuracy of the system. If multiple positional body markers are used, not all of them need to be continuously tracked. The positional body markers may be surface markers, attached at the skin, or may be internal markers, endocavitary, endoluminal or otherwise placed in the body at a known position. A known internal structure, like vessel crossing, may also serve as an anatomical reference point but without the advantage of having the position continuously tracked.

Figure 3:
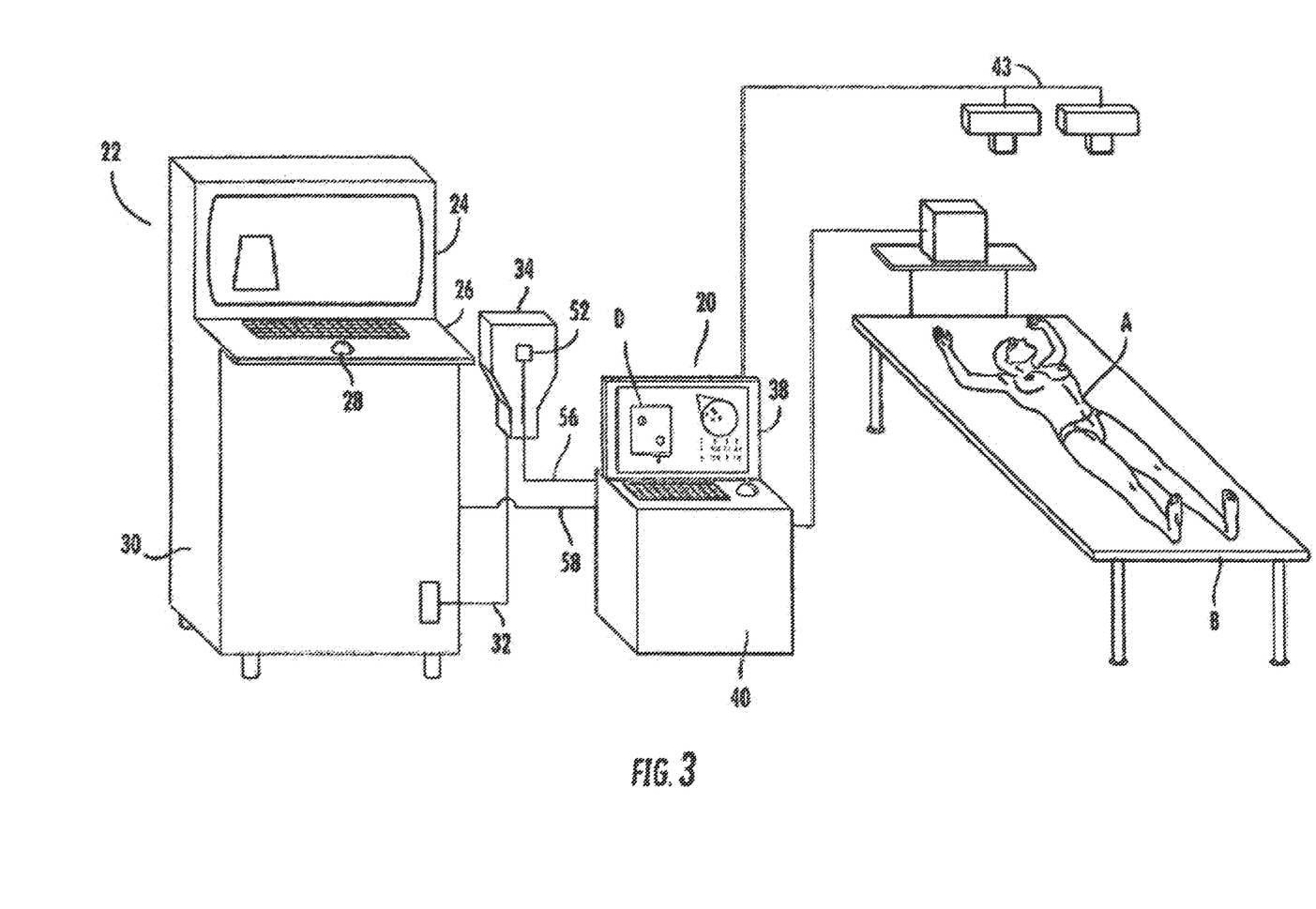
FIG. 3 depicts an alternate embodiment illustrating an overhead infrared or optical anatomical reference tracking system.

Other configurations will work as well. For non-limiting example, FIG. 3 illustrates an alternate configuration in which second magnetic sensor 52 provides the positional information to the TDMD 3D position board/module 60 (not seen in TDMD computer 40). The overhead infrared or optical anatomical reference (AR) tracking system 43 provides the positional information to the TDMD computer 40. Video output 24 from the ultrasound device 22 is digitized by the dedicated TDMD module/board 40. Again, analog to digital image conversion is not required if the ultrasound device 22 can be interfaced and directly provide the digital images to TDMD computer 40. The digital ultrasound images with the associated positional information are displayed in the TDMD computer display 38 or stored for review and processing at a later time.

Figure 4:
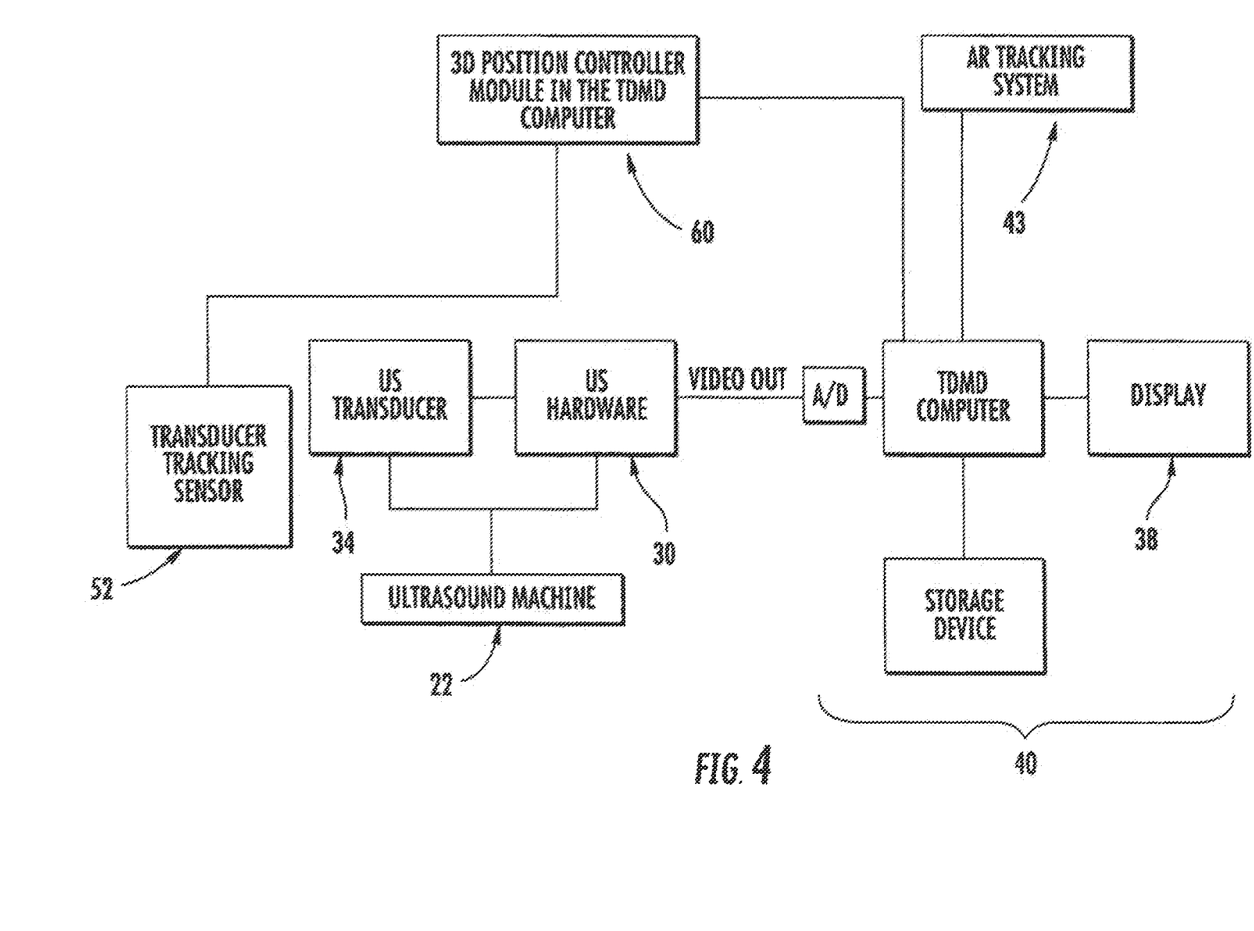
FIG. 4 illustrates the functional block diagram for the inventive device in the alternate embodiment with an overhead infrared or optical anatomical reference tracking system.

Turning to FIG. 4, a block diagram illustrating the various general working aspects of inventive device 20 are shown. Second magnetic sensor 52 provides the positional information to the TDMD 20 3D position board/module 60 and overhead infrared position detector 43 transmits positional information to TDMD computer 40. Video output 24 from ultrasound device 22 is digitized by the dedicated TDMD module/board 40. It should be noted that the analog to digital image conversion is not needed if the ultrasound machine can be interfaced and it can directly provide the digital images to the TDMD 22.

Figure 5:
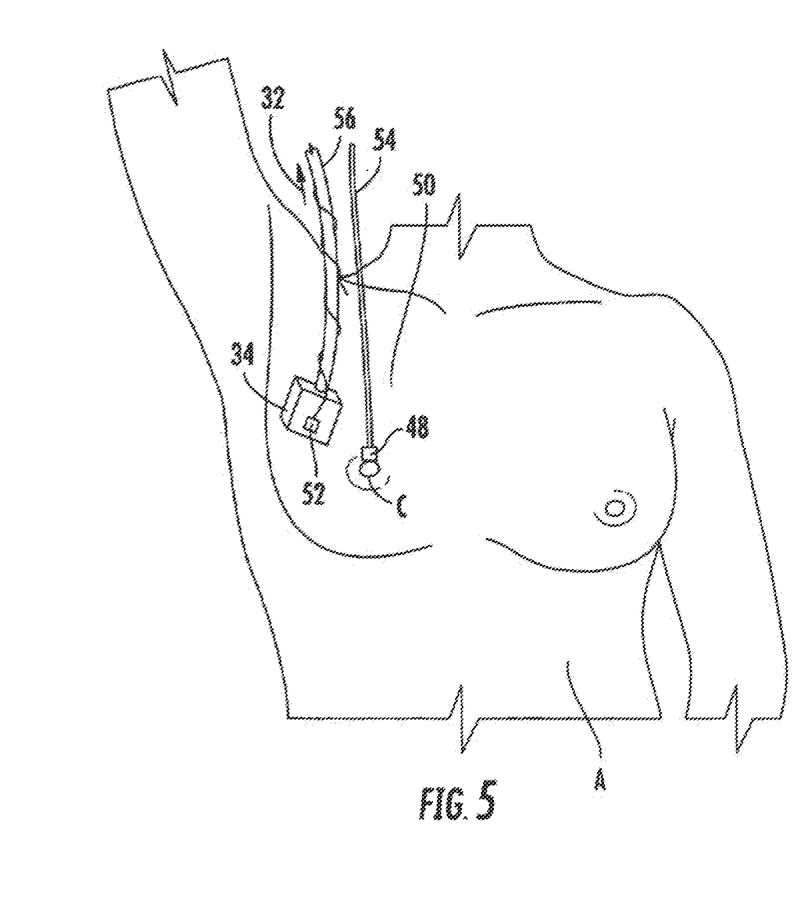
FIG. 5 depicts the inventive apparatus in a breast ultrasound exam.

Returning to FIG. 1, second magnetic sensor 52 is attached to the exterior of transducer 34 and, as seen in more detail in FIG. 5, first magnetic sensor 48 is positioned at the anatomical reference, here, the breast nipple C of Patient A.

Ultrasound device 22 video output 24 is directed to TDMD video capture board at TDMD Chassis 40 through video output cord 58 as is 3D magnetic tracking member 42 through 3D magnetic tracking member cord 46. TDMD display 38 is then enabled to shows images D captured by ultrasound device 22 and associated positional data as collected from 3D tracking member 42, first magnetic sensor 48 and second magnetic sensor 52.

Figure 6:
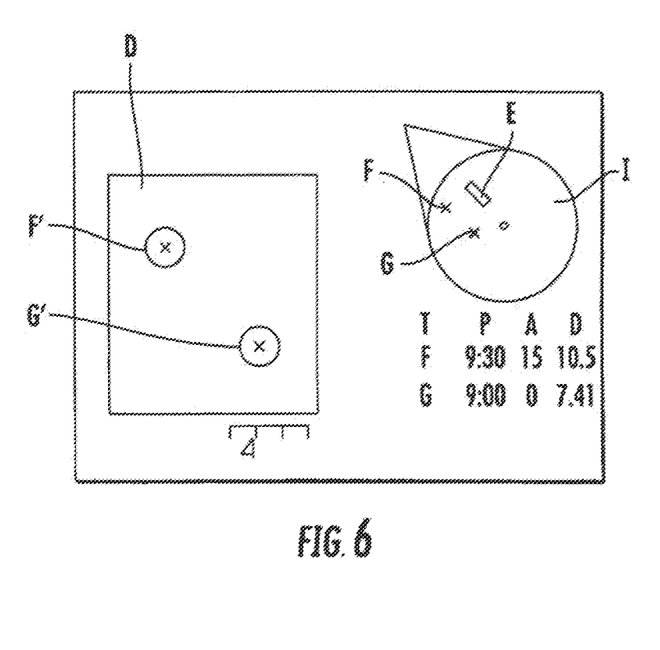
FIG. 6 depicts the image created during a breast examination as illustrated in FIG. 5.

Turning to FIG. 5, a detailed view of transducer 34 with the second magnetic sensor 52 and first magnetic sensor 48 applied at the upper margin of the right nipple. First magnetic sensor 48 continuously tracks the anatomical reference position, the nipple in this case, to compensate for motion artifacts during the ultrasound exam. FIG. 6 illustrates TDMD display 38 with the captured video image D from the ultrasound machine and the body diagram of FIG. 5 with the transducer 34 position and orientation at the time of image capture D and two different targets F and G in body part diagram I, and F' and G' as selected in image D image capture.

Additionally, each target, F and G, is displayed with the associated position (hourly representation or degrees to longitudinal axis and anatomical reference as center) and distance (cm) from the selected anatomical reference, nipple C. Positional coordinates are displayed under body part diagram I in FIG. 6. While the inventive device enable any number of coordinates to be displayed, here the example includes Target number (T), example F and G, Positional in reference to anatomical reference in hour format (here, 9:30 for F and 9:00 for G), position from anatomical reference point in degrees (here, 15° for F and 0° for G), and distance from anatomical reference point in centimeters(cm)(here, 10.5 cm for F and 7.41 cm for G). Also, transducer 34 position location is identified at transducer position Icon E.

Additionally, an additional display function is to show a cumulative area of the transducer positions (via icon E) over the body diagram, where the ultrasound images were recorded during patient examination. This will allow for the quick evaluation of an ultrasound examination completeness, at the time of examination or at a later time.

In the preferred embodiment, any off the shelf generic PC computer with Windows XP® (by Microsoft Corporation, Redmond, Wash.) can be used to run instructions compiled in C++ and dotnet languages. While preferred, those skilled in the arts will understand that the invention can be implemented on any other computer platform and operating system.

The software to run the program is that incorporated by reference above. The software substantially used to process the data received by the processor form the at least one sensor and data from the ultrasound to manipulate the data for identifying, and storing in memory as selected by the user, target site location and size information in relation to selected anatomical reference points for simultaneous review and interpretation and later retrieval for comparative purposes with later examination, whether compared in real time or a later time based upon saved data. The inventive device enabling a user to accurately review, evaluate, and compare examination results by having anatomical reference point guides to isolate target sites.

The body diagram representation is not limited to the "bird's eye view" type like the "clock" representation for the breast, but more complex and realistic three dimensional representations of the body or body regions, including images obtained using contour rendering algorithms, can be used. The calculated and recorded positional data can be displayed in these representations. The ultrasound transducer position, orientation, can be depicted in a realistic appearance in space so it can be easily reproduced at subsequent examinations.

Additionally, the preferred 3D position registration system is based on magnetic tracking technology (for example, like that manufactured by Ascension Technology, Burlington, Vt.); however, any other suitable technology, such as optical or ultrasound, may be employed. Moreover, the inventive device can be deployed as an add on to any existing ultrasound unit, and can outfit DICOM compatible and non DICOM machines as well. The infrared sensors, also commercially available (Natural Point inc., Corvallis, Oreg.), comprise at least one infrared cameras with the dedicated hardware and software receiving reflected infrared light from the reflectors applied over the anatomical references. The infrared cameras can be replaced with optical cameras and the infrared reflectors with optical markers. One or more infrared or optical cameras can also be used.

The ultrasound probe and anatomical reference point real time tracking is not limited to the above solution, but other tracking modalities like ultrasound, optical, inertial etc. can be used for the ultrasound probe and optical/pattern recognition, magnetic, etc. for the anatomical reference point real time tracking. It should also be noted that tracking modalities can be used in combination with one another, for non-limiting example, ultrasound tracking with optical tracking. It is also notable that the described TDMD system and method can optionally be used with the anatomical reference tracking feature disabled.

Figure 7:
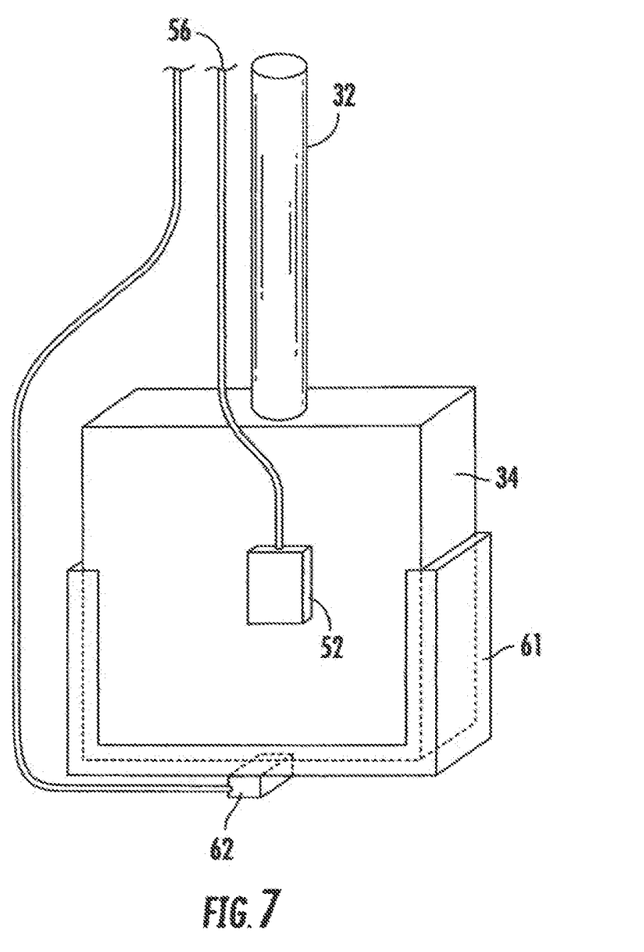
FIG. 7 illustrates the ultrasound transducer with the sensors in the calibrating tool.

In any of the above configurations, initial calibration is needed to register the ultrasound probe scanning plane orientation and position. The initial calibration may be performed with or without the use of a second positional sensor 62 (FIG. 7), however the use of a second magnetic sensor makes the calibration task easier and more precise. Without second positional sensor 62, scanhead center of transducer 34 and plane orientation need to be manually entered. This initial calibration is done once only, unless a different ultrasound probe is used or the fixed magnetic sensor position on the ultrasound transducer is modified. As those skilled in the arts will understand, there are many ways and methods to calibrate ultrasound equipment. For non-limiting example, one method includes placing ultrasound transducer 34 in a dedicated holder 61 which has the calibrating magnetic sensor 62 attached to correspond exactly to the center of the ultrasound transducer 34 scanning head, in a position aligned with the scanning plane of the transducer.

Figure 8:
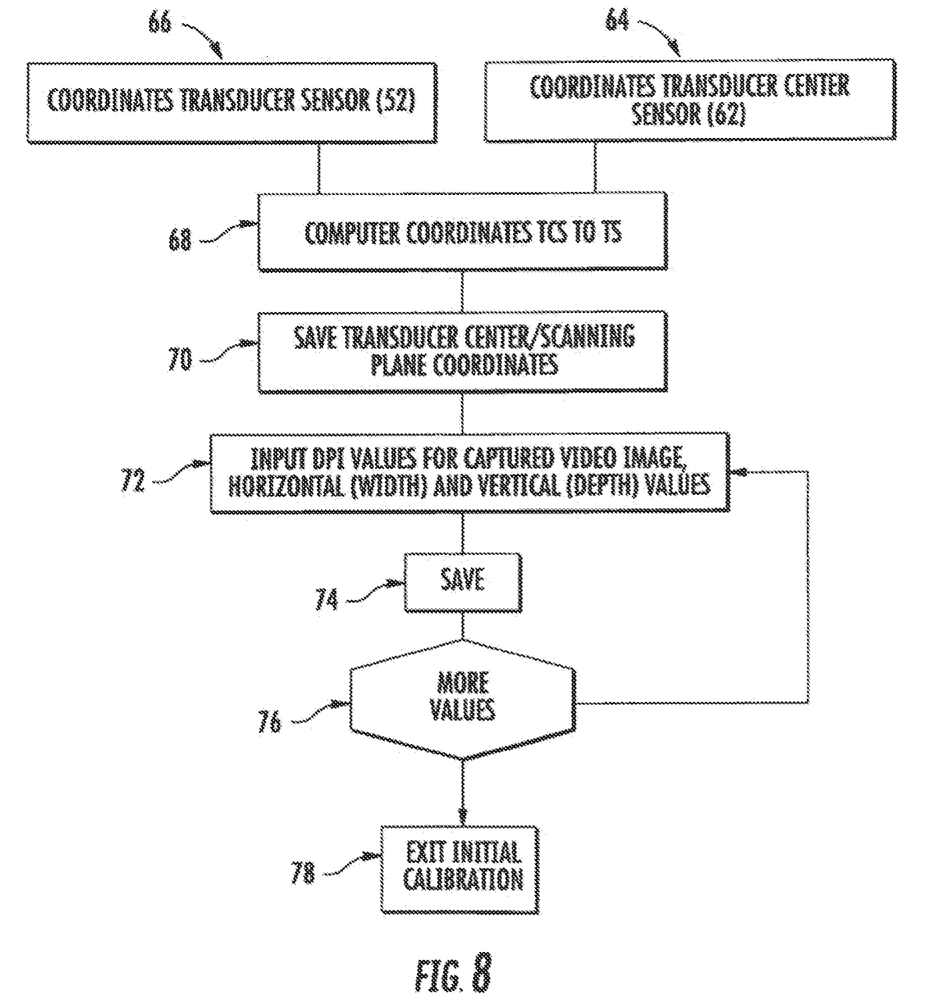
FIG. 8 illustrates the steps of initial calibration.

The initial system calibration steps are shown in FIG. 8. When performing the second magnetic sensor 52 calibration, TDMD computer 40 registers the 3D position of sensor 52 in relation to the center of the transducer 34 scanning head 64 and in relation to the transducer scanning plane 68, so it can accurately define the position of each pixel in the ultrasound image in relation to the transducer scanning head and first magnetic sensor 48. That coordinate is then saved 70. In addition to the above sensor initial calibration, the ultrasound image size calibration is needed for each transducer 72, in dots per inch (dpi) or per mm and it can be done automatically in systems where this information is passed from the ultrasound machine, 22, to the TDMD computer. For systems where this is not possible, the manual calibration for image size: depth and width, is needed and can be performed by manually entering the calculated values, obtained by dividing the number of pixels to the size of markers of known size in the ultrasound image. This information is then saved 74. The process is repeated 76 until all required values are calculated and saved 76. The initial calibration process is then exited 78.

Figure 9:
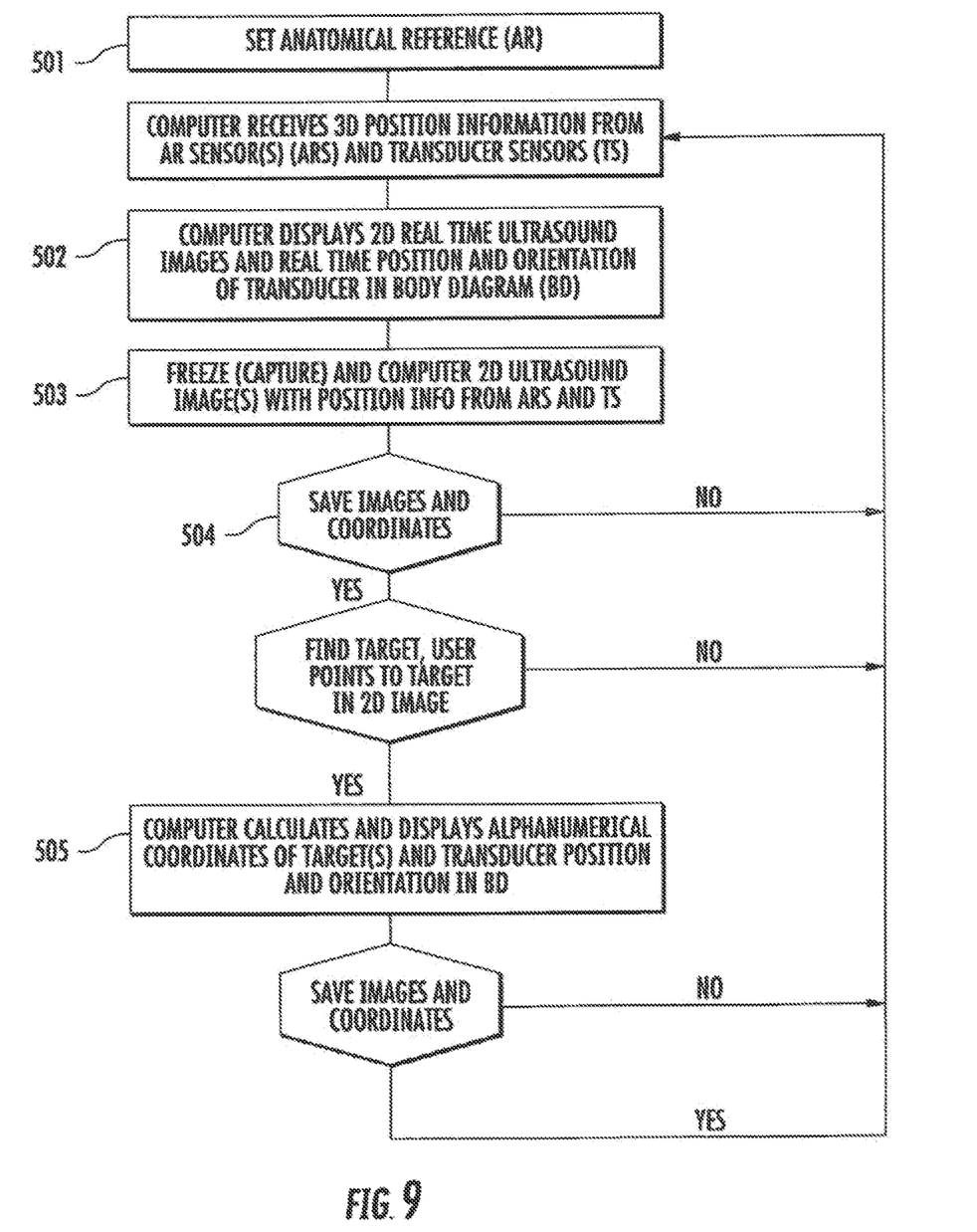
FIG. 9 illustrates the steps needed to measure and record the positional information associated with the diagnostic ultrasound images.

Turning to FIG. 9, the TDMD operation steps required to record the 3D position of targets in relation to anatomical reference points are shown. For each patient, at the beginning of examination the anatomical reference spatial position and the ultrasound probe orientation relative to the body is defined and recorded, 501. One method is to hold the ultrasound transducer scanhead center at the anatomical reference, for ex. on the nipple, with the transducer held in the preset orientation, ex. sagittal plane, horizontal, parallel to the patient and examination table long axis (FIG. 1). At least one anatomical reference point needs to be defined at the beginning of each examination, however more than one anatomical reference points can be defined, which can increase the measurements accuracy. When a second magnetic sensor is used to track the anatomical reference position, the first magnetic sensor 48 position in relation to the anatomical reference point is recorded and computed by the TDMD 40 during the anatomical reference setting step, so it can continuously track the anatomical reference point. This additional calculation is necessary when the first magnetic sensor 48 is applied in close proximity, but slightly off the selected anatomical reference. In other embodiments where the anatomical reference sensor or marker, for example when using the overhead anatomical reference tracking system with infrared reflectors or markers or optical markers, is applied exactly at the anatomical reference point, this additional correction is not necessary and can be skipped. If the magnetic anatomical reference marker can be applied exactly at the anatomical reference point, this additional correction is not necessary and can be skipped.

Continuing with FIG. 9, at 502 the transducer 34 position and orientation and anatomical reference point are continuously displayed in TDMD computer display 38 or ultrasound display 24, as a moving icon over the body part diagram, in reference to the anatomical reference point, with an "out of range" warning when the transducer is moved out of the scanning region range or too far from the magnetic transmitter. The frame images are entered and displayed in the TDMD display 38 or if implemented at the ultrasound machine host computer, ultrasound display 24. In the preferred embodiment, the ultrasound user can "freeze" the 2D still image of interest or capture short video cine loops or 3D images, 503 (FIG. 9). The "frozen" image or the video clip can be saved in TDMD computer 40 or a host computer with the positional information associated to each frame or set of frame images, in a local database, 504, (FIG. 9).

The coordinates associated with a target in a still image, in relation to the anatomical reference point, can be displayed by pointing to the target (image pixel/region of pixels) with a pointing device in the image displayed on the TDMD display 38 or Ultrasound display 24, step 505 (FIG. 9). The target position can be also determined at a later time in the same TDMD computer or a remote computer with the TDMD software, from the saved ultrasound images with the associated positional information. The target positional information can be displayed at the time of the ultrasound examination or at a later date, it also can be printed and stored in digital format at any time after the acquisition.

For the images in cine loops, the position display process is similar to the still images, after the cine loop is "frozen" at a certain frame. For 3D ultrasound probes, the same principle applies when a 2D image is reconstructed from the recorded 3D data and the positioning information is applied to the ultrasound 2D image.

The position of each pixel in an ultrasound image in reference to the anatomical reference(s) is calculated from the ultrasound probe tracking system data and corrections applied to the anatomical reference points from the secondary tracking system that monitors the anatomical reference points. Both tracking systems provide 3D positional data. The positional information displayed for each image is presented in alphanumerical format as distance and angle from the anatomical reference, hourly coordinates, where the position of a target is assigned an hour from 1 to 12 o'clock, when the region (breast or abdomen) is viewed from above as a clock, with the anatomical reference, nipple or umbilicus respectively, imagined in the middle of the clock and also as a graphic diagram of the region, see, e.g., FIG. 6. Additional data fields are also available, including the position of the patient during the examination (supine, lateral decubitus, etc). The graphic diagram points to the relative position of a target over a diagram of a body part, the breast, for example. Accordingly, it is easy to see that multiple targets can be selected/displayed or erased.

The TDMD computer allows for the manual or automatic entry and display of target coordinates from previous exams over the body diagram or body part diagram, with the ultrasound probe icon position and orientation in relation to the anatomical reference point and body axis, represented in real time in the diagram. This feature allows for ultrasound device operator orientation and guidance to help moving the ultrasound transducer and find a known target from a previous examination.

Accordingly, the present invention is a system and method where a target position in a human or animal body can be automatically recorded in reference to any preset anatomical reference point, when performing an ultrasound examination. The system allows for automatic correction for body or anatomical reference motion during the examination.

It is to be understood that while the invention has been described as being implemented on the ultrasound machine itself, it is capable of other deployments as well. For non-limiting example, it could be deployed at the level of a host computer or a separate computer from the ultrasound system where the separate computer is connected to the ultrasound machine so it can simultaneously display the image outputs from the ultrasound machine and the diagnostic image positional information in graphic and alphanumeric modes from the TDMD device. The information from the separate computer can be stored as hardcopy or it can be digitally stored.

It is also to be understood, that even though numerous characteristics and advantages of the preferred and alternative embodiments have been set forth in the foregoing description, together with details of the structure and function of the embodiments, the disclosure is illustrative only, and changes may be made in detail within the principles of the invention to the full extent indicated by the broad general meaning of the terms in which the appended claims are expressed.

What is claimed is:

1. An image registration system comprising:
an ultrasound imaging probe configured to acquire image data during a current examination, the image data calibrated to the ultrasound imaging probe;
a marker configured to identify an anatomical reference point on a patient body during the current examination; and
a processor programmed to:
detect an orientation of a body axis of the patient body relative to the ultrasound imaging probe;
record a position of the anatomical reference point relative to the ultrasound imaging probe;
record a position of the ultrasound imaging probe relative to the orientation of the body axis of the patient body;
track a realtime position of the anatomical reference point by monitoring a position of the marker during the current examination;
track a realtime position and orientation of the ultrasound imaging probe during the current examination relative to the realtime position of the anatomical reference point and the detected orientation of the body axis of the patient body; and
display the realtime position of the ultrasound imaging probe and the realtime position of the anatomical reference point as an overlay on a graphic diagram of the patient body during the current examination;
wherein the realtime position of the anatomical reference point is tracked independent from the orientation of the body axis of the patient body; and
wherein the ultrasound imaging probe is registered to the position of the anatomical reference point and to the orientation of the body axis of the patient body.

2. The image registration system of claim 1 wherein the marker comprises a magnetic sensor.

3. The image registration system of claim 1 wherein the marker comprises one of an optical marker and an infrared marker.

4. The image registration system of claim 1 wherein the imaging probe comprises a three-dimensional (3D) ultrasound probe.

5. The image registration system of claim 1 wherein the processor is further programmed to display the realtime position of the imaging probe as a position in reference to the realtime position of the anatomical reference point in an hourly coordinate system, with the anatomical reference point positioned in the center of the hourly coordinate system.

6. The image registration system of claim 1 wherein the processor is further programmed to display the position of the imaging probe as a moving icon on the graphic diagram of the patient.

7. The image registration system of claim 1 further comprising a magnetic sensor coupled to imaging probe; and wherein the processor is further programmed to calibrate a position of the magnetic sensor in relation to a scanning plane of the imaging probe.

8. The image registration system of claim 1 wherein the processor is further programmed to calculate a position of each pixel of the image data in reference to the anatomical reference point and a body axis of the patient.

9. The image registration system of claim 1 wherein the processor is further programmed to display the position and orientation of the imaging probe as a distance from the anatomical reference point relative to the orientation of the body axis of the patient body.

10. The system of claim 1 wherein the processor is further programmed to:
display coordinates of a target located in a previous examination over the graphic diagram of the patient body from the current examination; and
simultaneously display the realtime position and orientation of the imaging probe and the realtime position of the anatomical reference point in the graphic diagram from the current examination.

11. The image registration system of claim 1 wherein the processor is further programmed to:
record a position of a target in the patient body relative to the anatomical reference point and the orientation of the patient body; and
display the position of the target on the graphic diagram of the patient body.

12. The image registration system of claim 11 wherein the processor is further programmed to simultaneously display the position of the target as an overlay on a medical image of the patient body.

13. A method comprising:
recording a body axis relative to an imaging probe of an imaging system;
defining a position of an anatomical reference point on a patient relative to an imaging probe of the imaging system;
registering a position and orientation of the imaging probe relative to an orientation of the body axis of the patient and to the position of the anatomical reference point;
acquiring image data from the patient using the imaging probe during a first examination, the image data calibrated to the imaging probe;
reconstructing a first image of the patient from the image data, the first image comprising a plurality of pixels;
calculating a position of each of the plurality of pixels in the first image in reference to the anatomical reference point and the body axis of the patient;
identifying a target within the first image, the target corresponding to a lesion within the body of the patient;
displaying coordinates of the target relative to the position of the anatomical reference point on a display; and
displaying coordinates of the target relative to the body axis of the patient on the display.

14. The method of claim 13 further comprising:
detecting motion of the anatomical reference point during the first examination; and
generating corrected coordinates of the target based on the detected motion of the anatomical reference point.

15. The method of claim 13 further comprising aligning the imaging probe with a plane of the patient to register the orientation of the imaging probe relative to the body axis of the patient.

16. The method of claim 13 further comprising continuously displaying at least one of a position of the anatomical reference point and a position and orientation of the imaging probe during acquisition of image data on the display.

17. The method of claim 13 further comprising:
monitoring a distance between the anatomical reference point and the imaging probe; and
detecting and displaying an out-of-range indicator if the monitored distance exceeds a threshold.

18. The method of claim 13 further comprising displaying the target on a second image that differs from the first image, the second image reconstructed from image data acquired during a second examination.

19. The method of claim 13 wherein displaying coordinates of the target comprises displaying coordinates of the target in an hourly coordinate system, wherein the position of the target is assigned an hour from 1 to 12 o'clock and the anatomical reference point is defined as the center of the hourly coordinate system.

20. The method of claim 13 further comprising displaying a cumulative coverage area of the imaging probe for the first examination on a body diagram of the patient.

21. A system comprising:
an ultrasound system configured to acquire ultrasound data from a patient and reconstruct an image from the ultrasound data, the ultrasound system comprising an ultrasound transducer;
a first sensor coupled to the ultrasound transducer;
a second sensor configured for attachment to the patient; and
a tracking system coupled to the first and second sensors, the tracking system comprising:
a display; and
a processor programmed to:
define and record an orientation of the first sensor relative to a body axis of the patient at the beginning of an examination, thereby defining an orientation of the body axis of the patient relative to the ultrasound transducer at the beginning of the examination;
define and record a position of the second sensor relative to the ultrasound transducer;
monitor the orientation of the ultrasound transducer relative to the body axis via the first sensor during the examination; and
monitor a position of an anatomical reference point on the patient via the second sensor during the examination, the anatomical reference point physically distinct from the body axis of the patient;
wherein the ultrasound transducer is registered to the position of the anatomical reference point and to the orientation of the body axis of the patient.

22. The system of claim 21 wherein the processor is further programmed to correct motion in the image using the monitored position of the anatomical reference point.

23. The system of claim 21 wherein the processor is further programmed to:
monitor a distance between the position of the ultrasound transducer and the position of the anatomical reference point; and
output an alarm if the monitored distance exceeds a threshold.

24. The system of claim 21 wherein the processor is further programmed to record the monitored orientation of the ultrasound transducer relative to the body axis and the monitored position of the anatomical reference point for the image in a database.

25. The system of claim 21 wherein the processor is further programmed to record the monitored orientation of the ultrasound transducer and the monitored position of the anatomical reference point.

26. The system of claim 21 wherein the processor is further programmed to:
continuously monitor the position of the ultrasound transducer in reference to an anatomical reference point on the patient and the body axis of the patient; and
output the monitored position of the ultrasound transducer in reference to the anatomical reference point and the body axis to the display in realtime.

27. The system of claim 21 wherein the processor is further programmed to output at least one of the monitored position of the ultrasound transducer and the monitored position of anatomical reference point to the display in realtime.

28. The system of claim 21 wherein the processor is further programmed to record at least one of the monitored position of the anatomical reference point and a position of the plurality of pixels of the image in relation to the body axis of the patient in a database.

29. The system of claim 21 wherein the display further comprises:
a reconstructed ultrasound image of a region of interest of the patient;
a body part diagram of the region of interest;
a first marker overlaid on the reconstructed ultrasound image, the first marker indicating the position of a first target within the region of interest; and
a second marker overlaid on the body part diagram, the second marker indicating the position of the first target on the body part diagram.

30. The system of claim 29 wherein the processor is further programmed to record the position of the first target relative to the anatomical reference point in at least one of a plurality of still images and a plurality of frames of a video clip.

31. The system of claim 29 wherein the display further comprises:
a third marker overlaid on the reconstructed ultrasound image, the third marker indicating a position of a second target within the region of interest; and
a fourth marker overlaid on the body part diagram, the fourth marker indicating the position of the second target on the body part diagram.

32. The system of claim 29 wherein the display further comprises hourly coordinates of the position of the first target in a coordinate system that defines the position of the first target relative to the anatomical reference point and the body axis of the patient, wherein the hourly coordinates reflect the position of the first target as a distance and an angle from the anatomical reference point, which is at the center of the coordinate system.

* * * * *